(12) United States Patent
Godoy et al.

(10) Patent No.: US 6,772,656 B2
(45) Date of Patent: Aug. 10, 2004

(54) SCREW TIGHT TUBE VICE FRAME

(76) Inventors: Arthur Alexander Godoy, 205 Santa Ana Ave., Long Beach, CA (US) 90803; Stephen Andrew Godoy, 205 Santa Ana Ave., Long Beach, CA (US) 90803

(*) Notice: Subject to any disclaimer, the term of this patent is extended or adjusted under 35 U.S.C. 154(b) by 0 days.

(21) Appl. No.: 10/025,632

(22) Filed: Dec. 26, 2001

(65) Prior Publication Data

US 2002/0083798 A1 Jul. 4, 2002

Related U.S. Application Data

(60) Provisional application No. 60/258,967, filed on Jan. 2, 2001.

(51) Int. Cl.[7] .................................................. B43K 5/00
(52) U.S. Cl. ........................................ 81/9.22; 606/186
(58) Field of Search ........................... 81/9.22; 606/186; 30/362; 285/340, 341

(56) References Cited

U.S. PATENT DOCUMENTS

| | | | | |
|---|---|---|---|---|
| 3,972,547 A | * | 8/1976 | Itoya ........................... 285/341 |
| 3,986,737 A | * | 10/1976 | Krusche ....................... 285/341 |
| 4,159,659 A | * | 7/1979 | Nightingale ................... 81/9.22 |
| 4,204,438 A | * | 5/1980 | Binaris et al. ................ 81/9.22 |
| 4,671,277 A | * | 6/1987 | Beuchat ....................... 81/9.22 |
| 4,771,660 A | * | 9/1988 | Yacowitz ...................... 81/9.22 |
| 5,279,552 A | * | 1/1994 | Magnet ........................ 81/9.22 |
| 5,401,242 A | * | 3/1995 | Yacowitz ...................... 606/186 |
| 5,551,319 A | * | 9/1996 | Spaulding et al. ............. 81/9.22 |

* cited by examiner

*Primary Examiner*—D. S. Meislin

(57) ABSTRACT

An apparatus is disclosed for attaching a needle housing or tube to the frame of a tattoo machine which facilitates cleaning and sterilization. The apparatus, or tube vice, comprises a tube which houses a needle which moves in and out of the subject's skin during tattooing, a hollow cylinder, a split ring ferrule and a compression nut. The tube is inserted into the hollow cylinder and the ferrule slides over the tube. The ferrule, nut and the hollow cylinder have beveled edges which mate. The nut slides over the tube to screw onto the hollow cylinder thereby compressing the ferrule against the tube without bending or crimping the tube. A tube grip may be attached to the tube. A method of manufacturing the tube vice is also disclosed. The tube vice can be provided in kit format.

1 Claim, 4 Drawing Sheets

SCREW TIGHT TUBE VICE FRAME

CROSS REFERENCE TO RELATED APPLICATION

This Application claims benefit from the Provisional Application No. 60/256,967 filed Jan. 2, 2001.

FIELD OF THE INVENTION

This invention relates generally to the field of tattooing and tattoo machines. More particularly, the invention relates to an apparatus for securing the tube grip, which houses the needle bar and needle grouping, to the frame of a tattoo machine or intradermal injection device.

BACKGROUND OF THE INVENTION

Tattoo machines necessarily break the skin of the subject during the tattooing process, causing a risk of the spread of infectious diseases such as Hepatitis, HIV and ADS. The standard in the industry therefore is to sterilize the tattoo machine before each use. In order to effectively and efficiently sterilize a tattoo machine, the components of the machine must be easy to remove, sterilize, and reassemble.

Prior art tattoo machines typically have a needle or needle grouping which extends through the tattoo machine frame and is driven by a motor to reciprocate linearly. A hollow cylinder or tube is attached to the tattoo machine frame and the needle grouping passes through the tube. A portion of the tube, often having a larger external diameter than the rest of the tube, has a gnarled outer surface. This portion is called a tube grip. The tube grip provides a gripable portion for the tattoo machine operator and also serves to guide the needle grouping and restrain lateral movement of the needle grouping. The tube grip and needle grouping must be removable to allow them to be cleaned and sterilized. On all modern tattoo machines, the tube grip is a removable part.

Existing tattoo machine technology employs several methods to secure the tube grip to the tattoo machine frame which tend to bend or crimp the cylindrical tube grip. The present apparatus available not only tend to damage the tube grip, but are slow to remove and reinstall, and apparatus with multiple small screws are difficult to sterilize.

A more recently developed method of attaching the tube to the frame is a split portion of the frame which partially encircles the tube and is tightened with a wing nut. Tattoo machines are covered with a light plastic bag during operation to avoid contamination or cross-contamination between the operator and subject. Not only are such bags often ripped by the protruding wing nut, but the tattoo machine is rendered less streamline by the frame extension, wing nut and bolt required. The wing nut type vice does not apply pressure evenly to the tube grip, and may result in bending or crimping of the tube grip.

BRIEF SUMMARY OF THE INVENTION

It is an object of the present invention to provide a secure, easy to assemble and disassemble and streamlined apparatus for attaching the tube grip and the tube housing needles in a tattoo machine to the frame of the tattoo machine in a manner that improves on the methods currently employed by tattoo machines.

It is a further object of the invention to provide a screw tight tube vice frame comprising a frame, a compression nut, a compressible ferrule and a receiving piece and a tube adapted such that the tube housing at least one needle may be inserted in the receiving piece, the ferrule slipped over the tube, and the nut slipped over the tube and pushed up against the ferrule, then screwed onto the receiving piece such that the ferrule is compressed and grips and retains the tube without bending or crimping it.

It is yet a further object of the present invention to provide a tube vice frame that allows rapid and easy removal of the tube grip, tube and needle groupings to allow for cleaning and sterilization. It is a further object of the present invention to provide a tattoo machine with a streamlined profile that is easily shrouded in plastic or other material without tearing the shroud.

Another object of the present invention is to provide an apparatus for securing a tube grip to be secured to or removed from a tattoo machine frame with a simple twist of a nut.

Another object of the present invention is to provide a method for manufacturing a screw tight tube vice frame that is efficient, inexpensive and creates a streamlined, easy to use vice frame on a tattoo machine which may be retrofitted to an existing tattoo machine.

DETAILED DESCRIPTION AND PREFERRED EMBODIMENT

Figure 1:
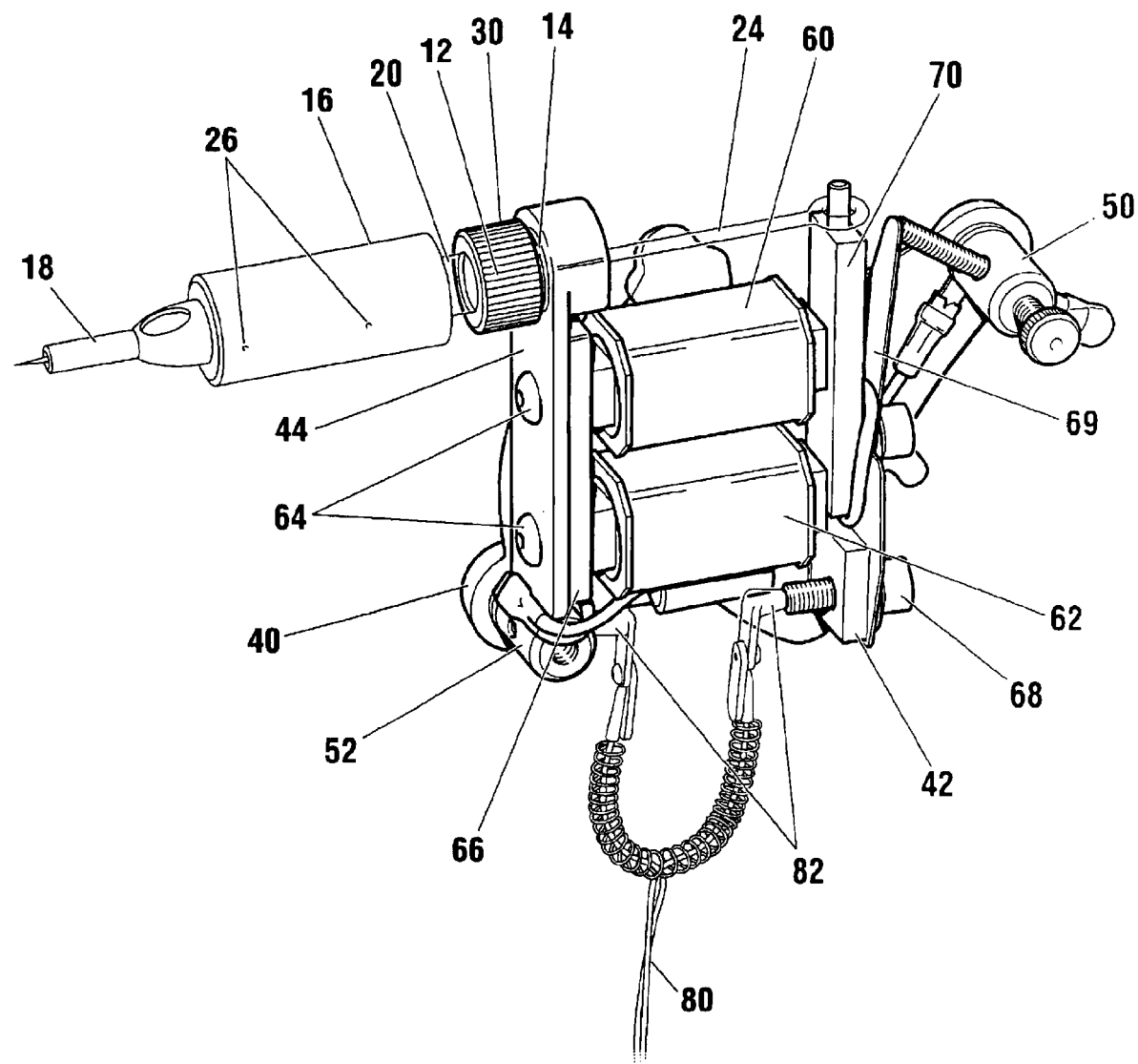
FIG. 1 is a perspective view of a tattoo machine with a screw tight tube vice frame according to the invention.

FIG. 1 depicts the preferred embodiment of the apparatus for attaching a tube 20 and associated components to a frame 40 in a tattoo machine 100 in accordance with the present invention. Tattoo machines 100 are generally comprised of a frame 40, typically made of metal. Standard frames 40 have a lower binding post 52 and an upper binding post 50. There is also typically a coil mounting bracket 44 at the front portion of the frame 40, and a spring saddle 42 at the lower rear portion of the frame 40. At least one electromagnetic coil 60 is mounted on the coil mounting bracket 44. Preferably there are two coils, a front coil 60 and back coil 62. An armature bar 70 is attached to a spring 69 which extends from the spring saddle 42 and is adapted to reciprocate when AC power is applied to the electromagnetic coils 60 and 62 such that the armature bar 70 is alternately attracted and repelled by the coils 60 and 62, as is known in the art.

Also as is known in the art, a needle bar 24 is attached to the armature bar 70 and passes through the coil mounting bracket 44 to maintain stability. The needle bar 24 has at least one needle attached to the needle bar tip (not shown). A hollow housing or tube 20 is placed over the needle bar 24 to guide the reciprocating needle bar 24. The present invention relates generally to an apparatus for securing the tube 20 to the frame 40 of a tattoo machine 100, referred to herein as the screw tight tube vice frame 30.

A hollow threaded rod 14 extends from the mounting bracket 44 towards the active end or front of the tattoo machine 100. The tube 20 is inserted into the hollow rod 14. A compression ferrule (not shown) comprising a hollow split ring with beveled edges is slipped over the tube 20 to abut the inner surface of the hollow rod 14. A compression nut 12 with an internal taper is then slipped over the tube 20 to abut and surround the ferrule (not shown) and screw onto the rod 14 thereby securing the tube 20 to the frame 40.

A tube grip 16 consisting of a hollow cylinder with a gnarled outer surface, which is a known tattoo machine component, is the slipped over the tube 20 the tube grip 16 may also be an integral component of the tube 20. A tube tip 18 is then inserted in the open end of the tube grip 16. The tube tip 18, tube 20, and tube grip 16 are connected as a unit.

Figure 2:
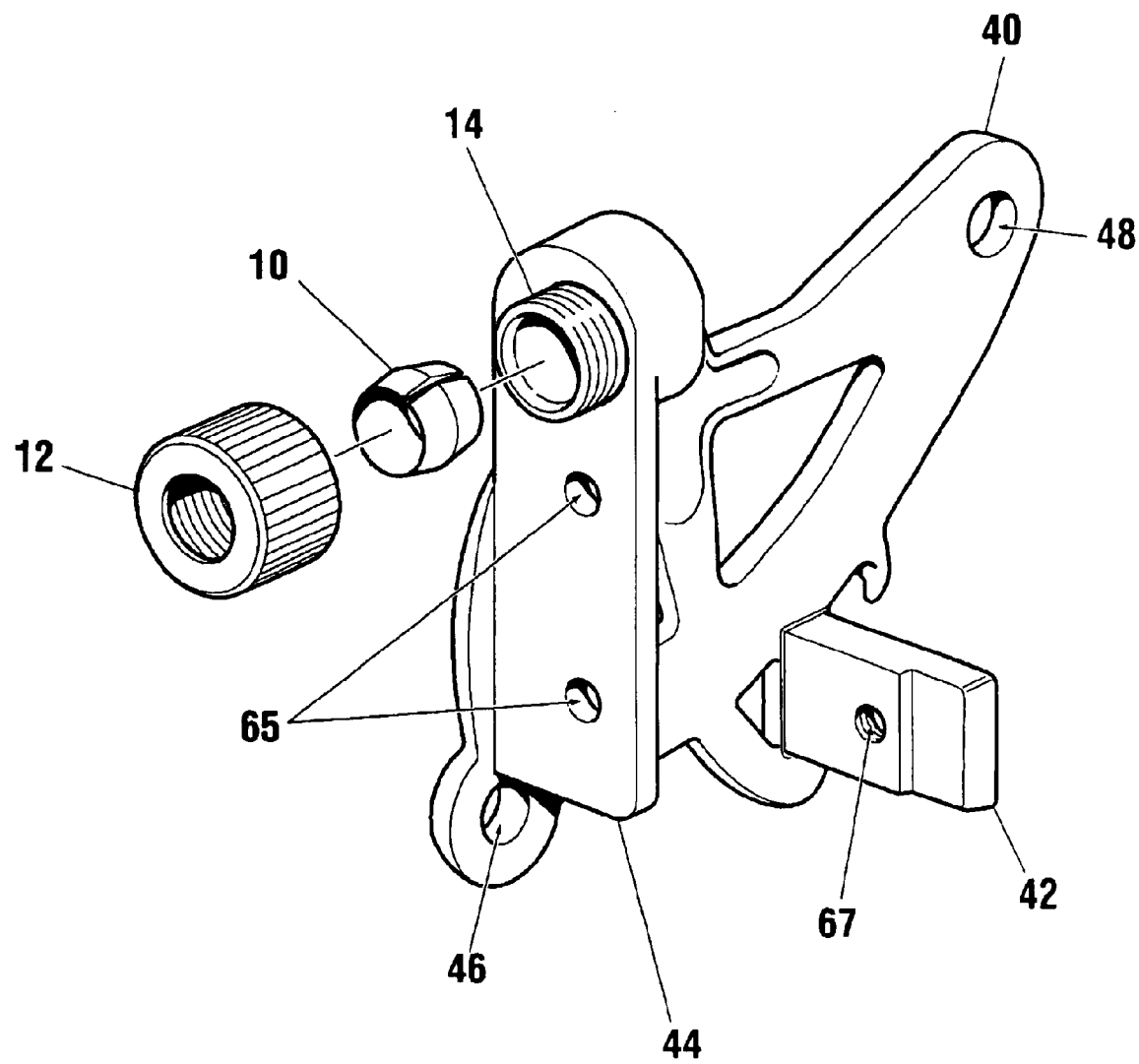
FIG. 2 is an exploded perspective view of the key components of the screw tight tube vice frame in detail.

Referring now to FIG. 2, an exploded perspective view of the key components of the screw tight tube vice frame are shown in detail. The tube vice mechanism, which is used to attach a tube grip of standard industry measurement to the frame, is located on the front lower portion of the frame. The frame 40 is shown fully exposed without the additional tattoo machine 100 components. The lower binding post hole 46 and upper binding post hole 48 are shown. In the preferred embodiment the hollow cylinder or rod 14 is removable from the frame 40. The inside surface of the rod 14 is internally tapered.

The compression ferrule 10 is a split ring or hollow cylinder preferably composed of a malleable metal such as brass. The ferrule 10 is tapered from each end to a central high point about the mid circumference of the ferrule 10. The ferrule 10 compresses as pressure is applied to the tapered ends such that the internal diameter of the ferrule 10 is reduced and the split or gap gradually reduced. The tapered ends of the ferrule 10 are preferable machined to the same angle as the taper on the interior surface of the rod 14, such that a mirrored mating surface is created between the ferrule 10 and rod 14.

The ferrule 10 is compressed between the rod 14 and the compression nut 12, which is a nut having interior threads matching those on the exterior surface of the rod 14, and preferably has a gnarled or otherwise textured exterior surface to provide a grip to the operator. The nut 12 also has an internal taper matching or mirroring that of the ferrule 10. The compression nut 12 is rotated in a clockwise direction to compress and lock the ferrule 10 in place.

The rod 14 is between approximately ½" to ⅝" in length and has a ½20 threading, with an inside diameter of either 5/16" or 11/64".

The compression ferrule 10 is optimally ¼" in length, with an inside diameter of 5/16 in an uncompressed state. The compression nut 12 must be sized to screw onto the rod 14.

The screw tight tube vice frame components may be manufactured from metal (such as aluminum, brass, steel, or iron) or any other rigid material (such as plastic, fiberglass, or lexan). A malleable metal such as brass is used. Holes are drilled in the tube vice frame 40 as follows: a hole for the upper binding post, a hole for the lower binder post, two holes drilled in the coil mounting bracket to accept the screws 64 that secure the coils 60 and 62 and a drilled and tapped hole for the spring screw 68 that secures the spring 69 to the frame 40.

An internal taper is machined into the front entrance of the threaded rod 14, starting at the outside diameter and machining inwards to a depth which is optimally ⅛". The threaded rod 14 is tapered internally to approximately the same degree as the compression ferrule 10 to allow the rod 14 to house the ferrule 10. The threaded rod 14 is attached to the tube vice frame 30 by machining the coil mounting bracket 44 on the frame 40 as follows: 1. step-drilling a primary hole measuring approximately 29/64" in diameter two-thirds of the way into the front lower section of the coil mounting bracket 44. 2. Drilling a secondary hole measuring approximately 5/16" or 11/64" in diameter through the remaining one-third of the coil mounting bracket 44 using the same center point as the previous hole. The primary hole is tapped with a ½20 bottoming tap from the entrance of the hole, starting at the front of the coil mounting bracket 44 and continuing through to the end of the step drilling (approximately two-thirds of the way into the coil mounting bracket 44).

The threaded rod 14 is screwed into the threaded hole (not shown) and protrudes approximately a ½" from the front of the frame coil mounting bracket 44.

In a variation to the preferred embodiment, the removable hollow threaded rod 14 may be cast or machined as part of the coil mounting bracket 44 on the frame 40, rather than as a removable component.

If the hollow threaded rod 14 is cast as part of the frame 40, it protrudes approximately a ½" from the front of the coil mounting bracket 44 (the same length as the threaded rod 14, described above, would protrude once screwed into the coil mounting bracket 44). If the frame 40 is cut on a CNC mill, the hollow threaded rod 14 may also be machined into the frame 40, protruding approximately ½" from the bottom of the frame 40. The same taper, machined to a recommended depth of ⅛" should be used whether a removable threaded rod 14 is used to house the compression ferrule 10 or the threaded rod 14 is cast or machined as part of the frame 40.

The exterior surface of the brass compression ferrule 10 is tapered on both ends with the tapers meeting in the middle of the ferrule 10. A slit is made vertically through the ferrule 10 to allow flexibility when it is compressed and tightened around the tube 20. The compression ferrule 10 is placed into the hollow section of the threaded rod 14 or machined frame component 14.

The compression nut 12 is step drilled, drilled, and tapered to the same specifications as the threaded rod 14. It may be machined from any type of metal. The nut 12 has interior threads adapted to be screwed onto the threaded rod 14 or threaded section 14 of the frame 40 that houses the compression ferrule 10 by turning the nut 12 in a clockwise motion to secure the tube 20, or conversely turning the nut 12 in an anti-clockwise direction to release the tube 20.

Figure 3:
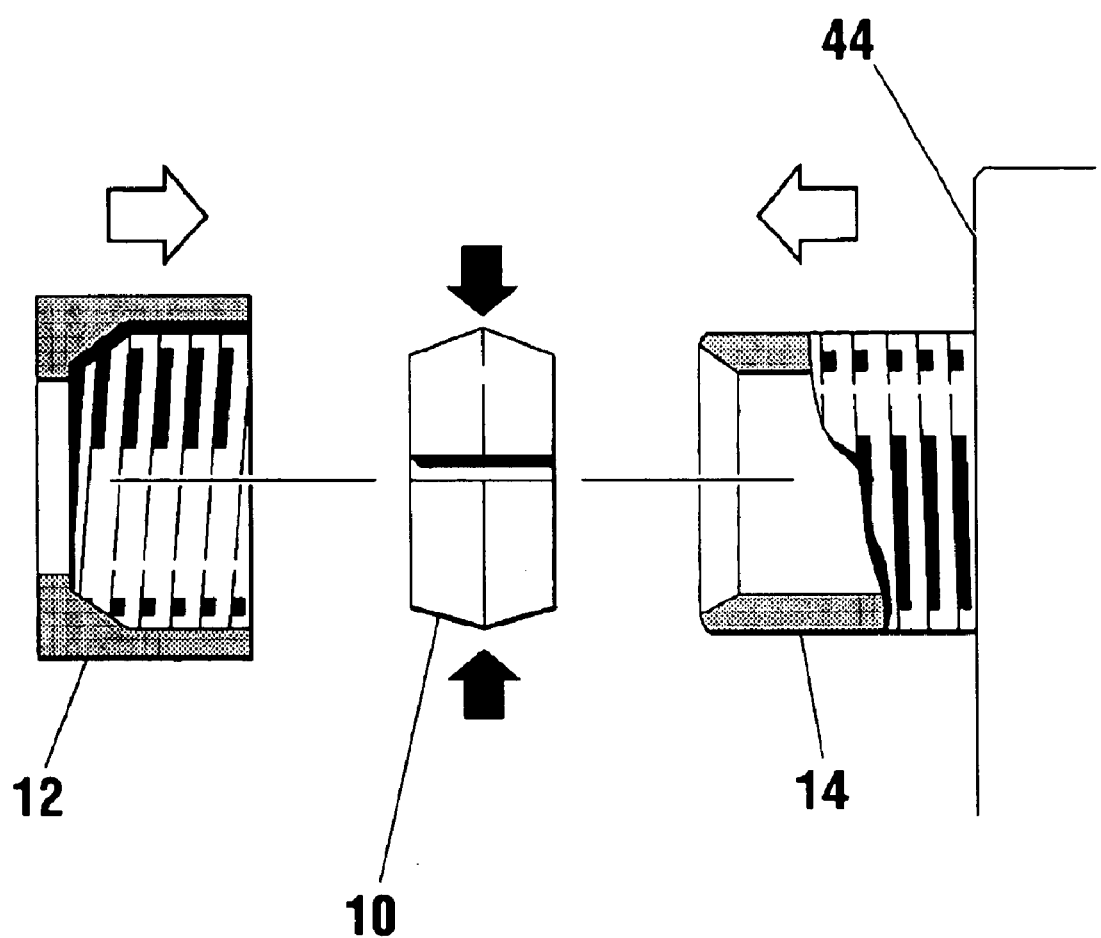
FIG. 3 is a pre-assembly side detail view of a compression nut, ferrule and threaded rod according to the invention.

Referring now to FIG. 3, a pre-assembly side detail view of a compression nut 12, ferrule 10 and threaded rod 14 is shown. The arrows indicate the direction of connection of the nut 12 to the rod 14. The tapered lip of the interior surface of the rod 14 serves to compress the ferrule 10 thereby reducing the interior diameter of the ferrule 10.

Figure 4:
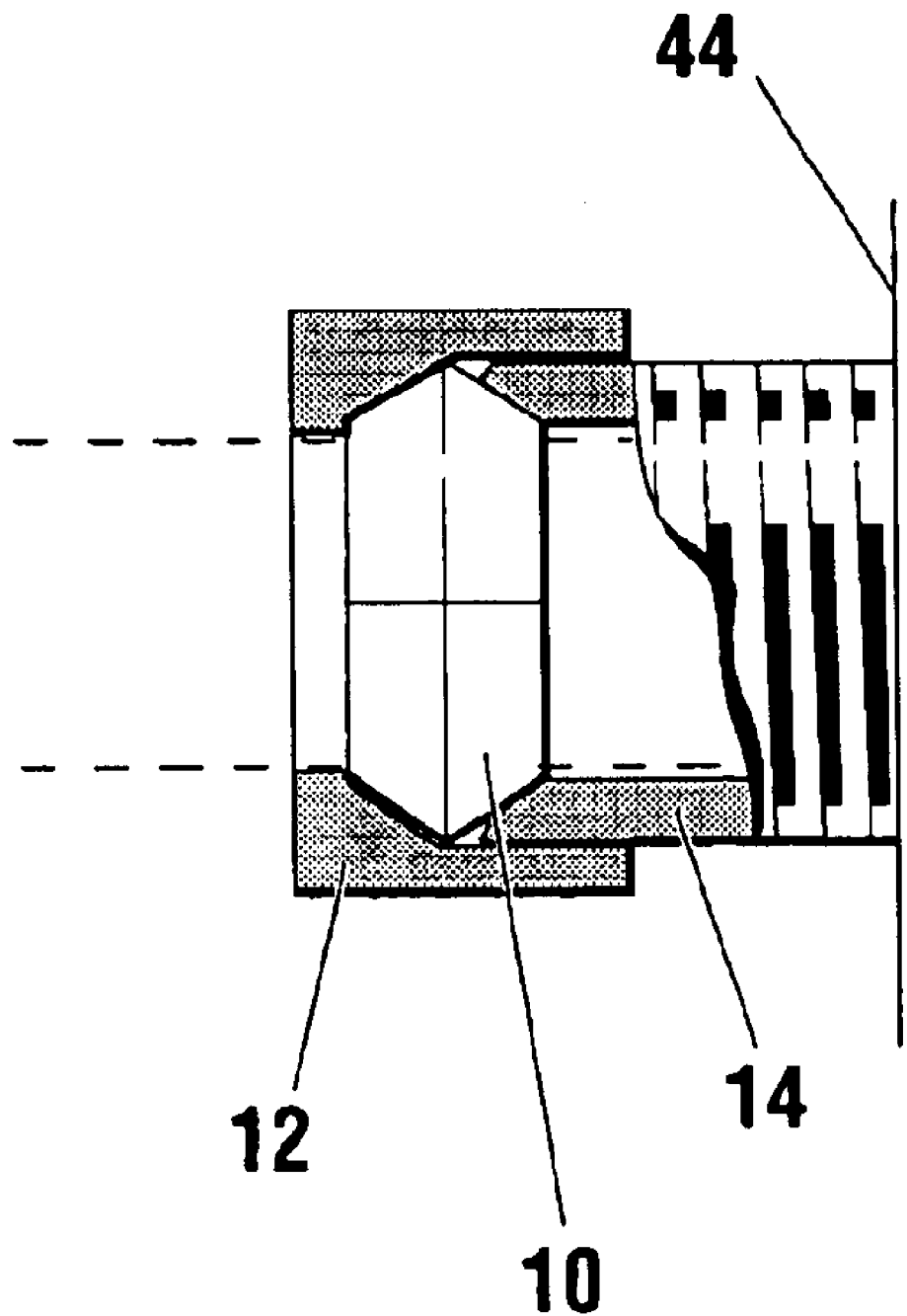
FIG. 4 is an assembled side detail view of a compression nut, ferrule and threaded rod according to the invention.

FIG. 4 shows an assembled side detail view of a compression nut, ferrule and threaded rod. The compressed ferrule abuts the tube 20 with its interior surface, thereby securing the ferrule 10 in place without bending, crimping or other damage to the tube 20.

In use, the sterilized, removable components are assembled as follows: the hollow rod 14 is screwed clockwise into the coil mounting bracket 44 on the frame 40, then the needle bar 24 is inserted through the frame 40 and attached to the armature bar 70. The tube 20 then slides over the active or distal end of the needle bar 24 and into the frame 40. The ferrule 10 slides over the tube 20 to seat against the distal end of the rod 14 and the compression nut 12 is tightened clockwise to compress the ferrule 10 against the tube 20 thereby retaining it in the frame 40. The tube grip 16 slides over the tube 20, and is secured. The tube tip 18 is then inserted inside the distal end of the tube grip 16 and over the needle bar 24, and is secured to the tube grip 16.

When the compression nut 12 is turned clockwise in a tightening motion, the bevels or tapers make contact and slide over each other, creating pressure evenly around the circumference of the taper on the compression ferrule 10 and causing it to compress. The vertical slit in the ferrule 10 provides a gap for compression as the ends of the slit move toward each other, creating a squeezing effect and securing the tube 20 to the frame 40 without bending or crimping it.

After use of the tattoo machine 100, the compression nut 12 is rotated counter-clockwise to relieve the pressure on the compression ferrule 10, resulting in the release of the tube 20. The motion is easy to perform and avoids damage to the tube 20 which commonly occurs in prior art tattoo machines 100. The present invention is a streamlined apparatus due to the low profile, inline ferrule 10, rod 14 and nut 12 arrangement.

The preferred embodiment and variations herein described are not intended to be exhaustive or to limit the scope of the invention to the precise forms disclosed. They are chosen and described to best explain the principles of the invention and its application and practical use to allow others skilled in the art to comprehend its teachings.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method of manufacturing a screw tight tube vice frame in a tattoo machine comprising the steps of:

(a) Drilling an internal taper into a hollow rod and cutting threads onto the exterior surface of said rod;

(b) Drilling a first hole into a tattoo machine frame but not completely through said frame, such that a portion of said frame remains;

(c) Drilling a second hole of a smaller diameter than said first hole through the remaining portion of said frame using the same centerline as said first hole, such that there is a transverse hole in said frame;

(d) Tapping said first hole;

(e) Screwing said rod into said first hole such that said rod protrudes from said frame;

(f) Machining a split ring ferrule with tapered ends of an angle equivalent to said internal taper of said rod;

(g) Machining a nut adapted to screw onto said rod with said ferrule between said rod and said nut such that said ferrule is compressed by said nut to retain objects disposed within said ferrule.

* * * * *